United States Patent [19]

Earley et al.

[11] Patent Number: 5,455,008
[45] Date of Patent: Oct. 3, 1995

[54] APPARATUS FOR ROBOTICALLY PERFORMING SANGER DIDEOXYNUCLEOTIDE DNA SEQUENCING REACTIONS USING CONTROLLED PIPET

[75] Inventors: James J. Earley, Upper Darby; Gerardus C. Tromp, Philadelphia; Darwin J. Prockop, Philadelphia; Sisko H. Kuivaniemi, Philadelphia, all of Pa.

[73] Assignee: Thomas Jefferson University, Philadelphia, Pa.

[21] Appl. No.: 287,105

[22] Filed: Aug. 8, 1994

Related U.S. Application Data

[63] Continuation of Ser. No. 962,285, Oct. 16, 1992, abandoned.
[51] Int. Cl.[6] .................................................. B01L 3/02
[52] U.S. Cl. .................. 422/100; 73/863.01; 73/864.24; 318/568.16; 422/63; 422/67; 935/87
[58] Field of Search .................................. 422/63, 67, 100; 935/87; 73/863.01, 864.24, 864.25; 395/93; 901/10, 46; 318/568.16

[56] References Cited

U.S. PATENT DOCUMENTS

| | | | |
|---|---|---|---|
| 3,853,011 | 12/1974 | Baumann | 73/864.24 |
| 4,483,382 | 11/1984 | Umetsu et al. | 422/63 |
| 4,715,413 | 12/1987 | Backlund et al. | 73/864.24 |
| 4,794,085 | 12/1988 | Jessop et al. | 422/63 |
| 4,818,492 | 4/1989 | Shimizu | 422/100 |
| 4,841,786 | 6/1989 | Schulz | 73/864.25 |
| 4,984,475 | 1/1991 | Uffenheimer | 73/864.22 |

FOREIGN PATENT DOCUMENTS

| | | |
|---|---|---|
| 0298669A1 | 1/1989 | European Pat. Off. . |
| 9116675 | 10/1991 | WIPO . |

OTHER PUBLICATIONS

Zymark Corp., "Zymate System User's Manual", Sections 1, 4.1, 4.3 and Appendices H, I, J (Oct. 1989).
Zymark Corp., "Hand User's Guide for the Zymate Xp Robot" (Apr. 1991).
Zymark Corp., "Proposal to Automate DNA Sequencing Assays" (May 1991).
Bente et al. "A Robotic Microassay System: Enzyme Linked Immunosorbent Assays (ELISA) in 96 well format" in Advances in Laboratory Automation Robotics 1986, Zymark Corp. Hopkinton Mass. 1987 pp. 201–215.
Eckstein et al. "Making a Turn Key ELISA Robot Work" in Advances in Laboratory Automation Robotics 1986, Zymark Corp. Hopkinton Mass. 1987 pp. 181–199.
Hahn, "Automated EIA Microplate Management System Applications of a Monoclonal Antibody Development Laboratory" in Advances in Laboratory Automation Robotics 1986, Zymark Corp. Hopkinton Mass. 1987 pp. 167–179.
Hamilton, "Robotic Assays for Fermentation Products" in Advances in Laboratory Automation Robotics 1986, Zymark Corp. Hopkinton, Mass. 1987 pp.1–21.

*Primary Examiner*—James C. Housel
*Assistant Examiner*—Jan M. Ludlow
*Attorney, Agent, or Firm*—Woodcock Washburn Kurtz Machiewicz & Norris

[57] ABSTRACT

A robotic system for performing nucleic acid sequencing reactions in microtiter plate format. The robot has a robot arm and its controller, robot hands with which it can manipulate microtiter plates with lids and microtiter plates without lids and with which it can perform pipetting in the 5 to 200 microliter range, cooled storage chambers with electronically controllable doors for storage of microtiter plates, cooled storage with an electronically controllable cover for storage of nucleic acid sequencing reagents, heating blocks to incubate the reactions at appropriate temperatures above ambient temperature, storage for boxes of micropipet tips, storage for microtiter plates in which sequence reactions will be performed and software for controlling the operation of the robot during pipetting.

26 Claims, 5 Drawing Sheets

APPARATUS FOR ROBOTICALLY PERFORMING SANGER DIDEOXYNUCLEOTIDE DNA SEQUENCING REACTIONS USING CONTROLLED PIPET

REFERENCE TO GOVERNMENT GRANTS

Research for this invention was supported in part by National Institutes of Health Grants AR38188 and HL45996. The United States government has certain rights in the invention.

This is a continuation of application Ser. No. 07/962,285, filed Oct. 16, 1992 now abandoned.

FIELD OF THE INVENTION

The present invention relates to the robotic execution of reactions to determine the DNA sequence of template DNA and more particularly to the robotic execution of Sanger dideoxynucleotide sequencing reactions.

BACKGROUND OF THE INVENTION

The genetic information for most living organisms is encoded by the molecule deoxyribonucleic acid (DNA). The genetic code is dependent on the chemical structure of the DNA. As described below, DNA is composed of four building blocks that are chemically bonded to one another to form long polymeric strands. Although DNA is composed of only four building blocks, successive addition of building blocks rapidly results in a structure with a unique sequence or combination of building blocks. The possible number of combinations formed by successive additions of building blocks rapidly becomes very large as it is the number of blocks to the fourth power.

Determination of the sequence of an organism's DNA and therefore determination of the sequence of the genes of that organism is essential to the understanding of biology and genetic disease.

The DNA of all higher living organisms exists in a double-stranded form that is composed of two complementary, anti-parallel polymeric chains, also called strands (hence double-stranded). Each of the chains is in turn composed of four building blocks called deoxynucleosides. Each deoxynucleoside is composed of a purine or pyrimidine ring structure called a base, a sugar moiety called deoxyribose and a phosphate group. The four deoxynucleosides are adenosine (A), cytosine (C), guanine (G) and thymidine (T). Deoxynucleosides are covalently attached to each other by phosphodiester bonds between the deoxyribose and the phosphate moieties to form the sugar-phosphate backbone of the strand. Because no bonds of the bases are a part of the structure of the backbone of the strand, the bases can be viewed as side-chains of the sugar-phosphate backbone. Each backbone has an orientation because the deoxyribose is an asymmetric molecule and the phosphodiester bonds are formed at hydroxyl groups at the number 3 and number 5 carbons. Conventionally, orientation is designated as 5' to 3' or 3' to 5'. The orientations of the two backbones of the double-stranded DNA molecule are opposite to each other and the strands are said to be anti-parallel.

The genetic information in DNA is encoded by the order or sequence in which the four deoxynucleosides are arranged in the polymeric chains. The order of deoxynucleosides in one chain determines the order of the deoxynucleosides in the opposite chain because the bases specifically interact with bases on the opposite strand to form stable complementary pairs of bases such that A pairs with T and C pairs with G. Because of the base-pairing it is possible to determine the sequence of one strand and infer the sequence of the complementary, anti-parallel strand.

DNA is synthesized in cells from building blocks that are deoxyribonucleotides. They are similar to deoxyribonucleosides but have a triphosphate moiety instead of the single phosphate found in deoxynucleosides. The two additional phosphates from the triphosphate moiety are released as by-products of the DNA synthesis reaction.

Determination of DNA sequences is of fundamental importance to understand biology and genetic diseases. It is estimated that organisms such as the mouse and man have haploid genomes that contain about 3 billion base pairs.

Advances in the chemistry of the reactions necessary to determine the sequence of DNA have considerably speeded up the process of obtaining DNA sequences as compared to even several years ago. Nonetheless, the reactions are labor-intensive.

Basically, the process of DNA sequencing comprises a series of steps: 1) preparation of the template, 2) performing reactions to generate a series of labeled fragments that begin at a defined point and that are terminated randomly at points where one of the bases occurs in the sequence, 3) separation of the randomly-terminated fragments according to size (length in nucleotides), 4) detection of the separated fragments, and 5) interpretation of the information contained in the pattern of separated fragments. The DNA sequencing reactions that are the subject of this application are those of step 2 above.

Two approaches are currently used to generate the randomly-terminated DNA fragments in step 2 above: (i) base-specific chemical modification of DNA followed by cleavage of the DNA at the sites of modification (Maxam and Gilbert) and (ii) termination of in vitro synthesized DNA by incorporation of synthetic nucleotide derivatives, called dideoxynucleotides (Sanger). The most widely used of these methods is the Sanger dideoxynucleotide method. It is also more amenable to automation since it involves conditions that are not as extreme, either in terms of physical or chemical conditions, as the Maxam and Gilbert chemical cleavage sequencing reactions.

Sanger dideoxynucleotide sequencing consists of annealing a short piece of synthetic DNA (called a primer) to template DNA and synthesis of new DNA by the addition of a DNA polymerase and deoxynucleosides under conditions of salts, pH, buffers and temperature that are appropriate for the DNA polymerase. Addition of dideoxynucleotides at concentrations appropriate for the DNA polymerase causes DNA synthesis to terminate. The termination occurs randomly but is a function of the ratio of the concentrations of the deoxynucleoside and the dideoxynucleotide forms of a particular base. A separate termination reaction is performed for each of the four bases. Each of the four reactions results in a collection of randomly-terminated fragments and together the four collections of fragments represent the sequence information attainable from the template/primer combination. DNA sequencing reactions are critical, time-consuming, labor-intensive and subject to fluctuation in efficiency from person to person.

Accordingly, it would be desirable to provide an apparatus for robotically performing DNA sequencing reactions.

SUMMARY OF THE INVENTION

It is an object of the current invention to provide an apparatus for robotically performing DNA sequencing reactions in an accurate and reproducible manner. This object, as well as other objects, is accomplished in a robotic system for automatically performing DNA sequencing, comprising (i) a robot controlled by a programmable controller and having an arm mounted for motion in vertical and horizontal planes, (ii) first and second robot hands, said first hand being adapted to carry an microtiter plate, said second hand being adapted for pipetting, a coupling disposed on said arm for attaching each of said robot hands thereto, (iii) heating units adapted to hold a microtiter plate, (iv) a plurality of work stations, each adapted to support a microtiter plate, (v) a reagent reservoir holding unit, containing a plurality of reservoirs, and (vi) a controlled temperature storage unit.

DESCRIPTION OF THE PREFERRED EMBODIMENT

Figure 1:
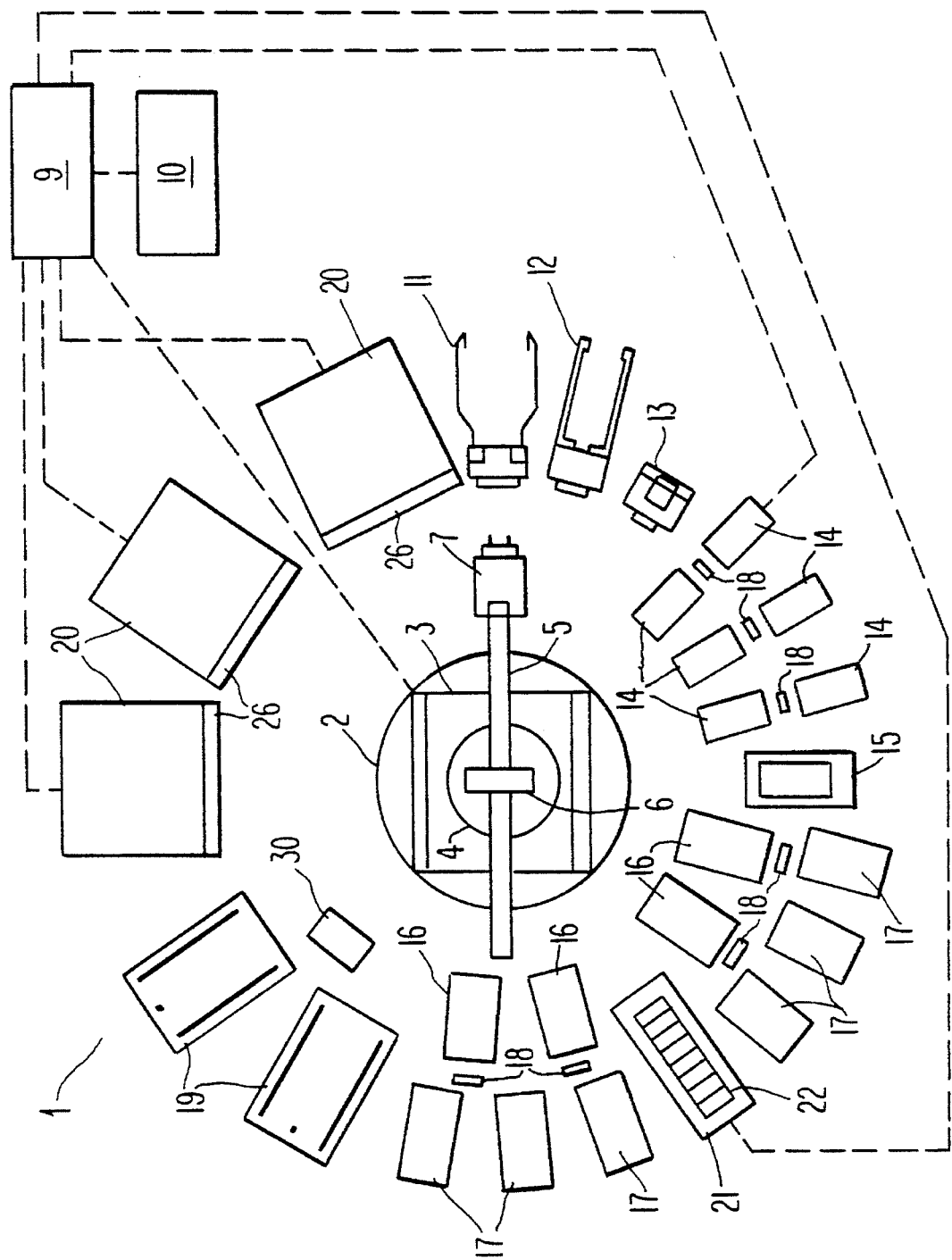
FIG. 1 is a plan view of the overall robotic DNA sequencing apparatus according to the current invention.
Figure 2:
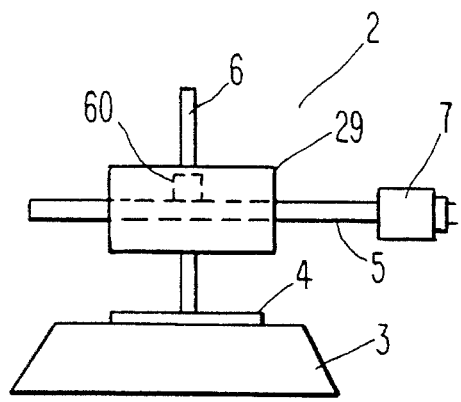
FIG. 2 is an elevation of the robot show in FIG. 1.

FIG. 1 shows an overall view of the robotic DNA sequencing system 1 of the current invention. The system includes a robot 2 controlled by a controller 9. The controller 9, which contains a programmable microprocessor, interfaces with a personal computer 10 that allows the operator to initiate and otherwise supervise the operation of the system. However, once initiated, the system is designed to operate automatically until all of the DNA samples have been processed. Such robots are commercially available and may be purchased from the Zymark Corporation. As shown in FIG. 2, the robot 2 is comprised of an arm 5 slidably mounted for horizontal motion in a housing 29. The housing 29 is slidably mounted for vertical motion on a support shaft 6 that is attached to a rotatable swivel plate 4 supported on a base 3. This arrangement provides the robot 2 with a cylindrical work space defined by rotation through approximately 376°, a 35 cm range of movement in the vertical direction, and a radial extension of about 65 cm in the horizontal direction.

A coupling 7 is disposed at the end of the arm 7 and allows a variety of general and special purpose "hands" to be installed onto the arm 5. In the current invention, these hands include a light duty hand 11, a heavy duty hand 12, and a specialized multichannel pipet hand 13. This last hand is shown in detail in FIG. 8.

Referring again to FIG. 1, the system also includes six heater blocks 14, various pipet wash stations 18, a pipet tip station 15, microtiter plate work stations 16, microtiter plate storage units 17, a reagent reservoir holding unit 21, pipet storage units 19, microtiter plate controlled temperature storage units 20, and a pipet disposal station 30.

Figure 3:
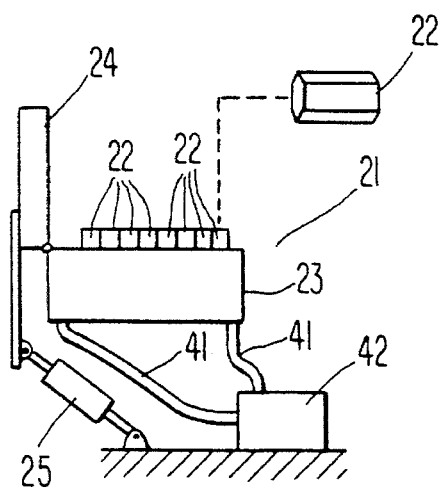
FIG. 3 is an elevation, partially exploded, of the reagent reservoir shown in FIG. 1.

As shown in FIG. 3, the reagent reservoir holding unit 21 is comprised of a cooling tank 23 to which cooled water is circulated from a cooling and pumping unit 42 via hoses 41. In the preferred embodiment, the cooling water is maintained at approximately 4° C. The tank is capable of holding and cooling eight reagent reservoirs 22. In addition, a lid 24 is provided that is operated by a pneumatic operator 25 electrically controlled by the robot controller 9.

Figure 4:
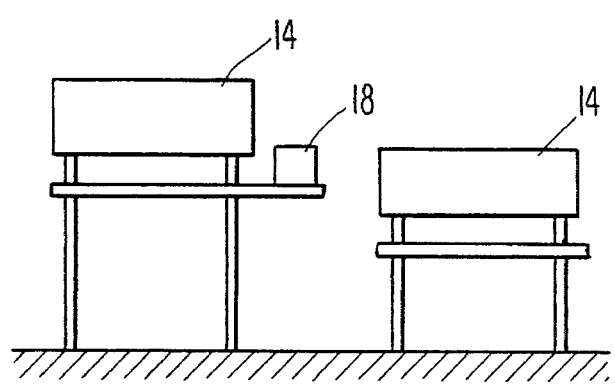
FIG. 4 is an elevation of two of the heater blocks shown in FIG. 1.
Figure 5:
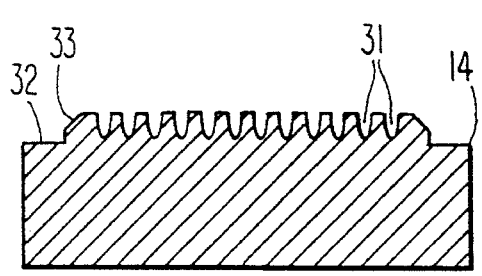
FIG. 5 is a longitudinal cross-section through one of the heater blocks shown in FIG. 4.

The heating blocks 14, two of which are shown in FIG. 4, employ heating elements (not shown), which may be resistance heaters. As shown in FIG. 5, each heating block 14 has a sculptured upper surface in which ninety six troughs 31 are formed. The troughs have approximately the same size, shape and layout as the outside surfaces of the wells 40 of a plastic standard microtiter plate 34, shown in FIGS. 7 and 8. In addition, the heating blocks 14 have a flat support surface 32 adjacent the sculptured upper surface that is adapted to stably support the edges of a microtiter plate 34. The heating blocks 14 also feature beveled edges 33 that are adapted to guide the microtiter plate onto the sculptured surface. In the preferred embodiment, the heating blocks 14 maintain the contents of a microtiter plate 34 at approximately 65° C.

Figure 7:
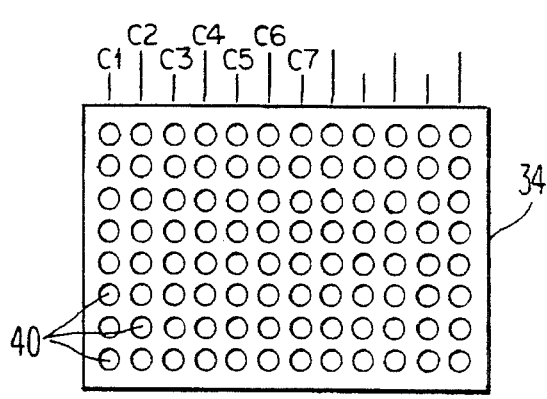
FIG. 7 is a plan view of a microtiter plate.
Figure 8:
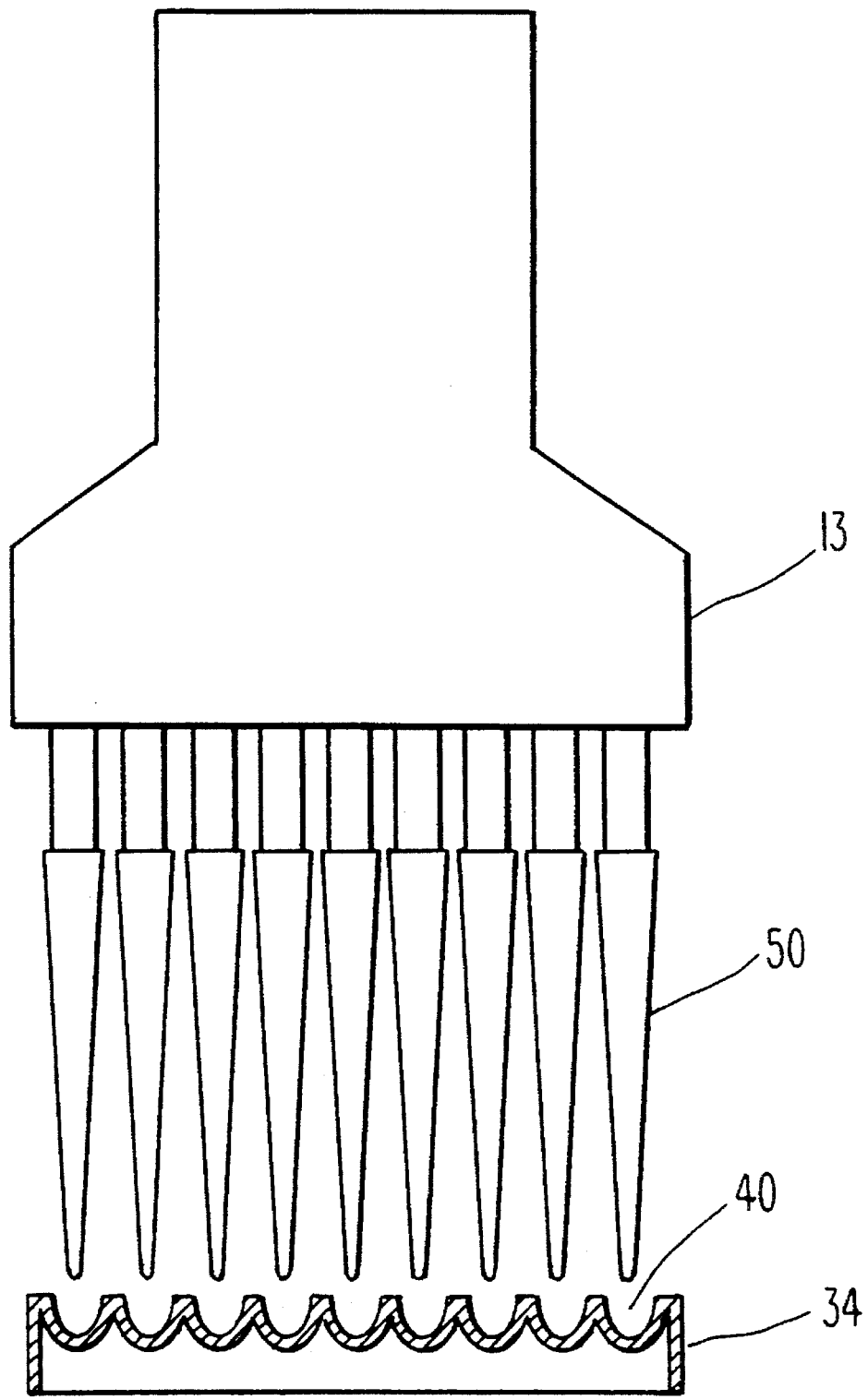
FIG. 8 is an elevation showing the multichannel pipet suspended above a microtiter plate.

As shown in FIGS. 7 and 8, standard ninety six well microtiter plates 34 are utilized, with each well having a capacity of about 300 µl. The wells 40 are arranged in twelve columns, with eight wells in each column. In the preferred embodiment, only the first seven columns C1 to C7 are utilized.

Figure 6:
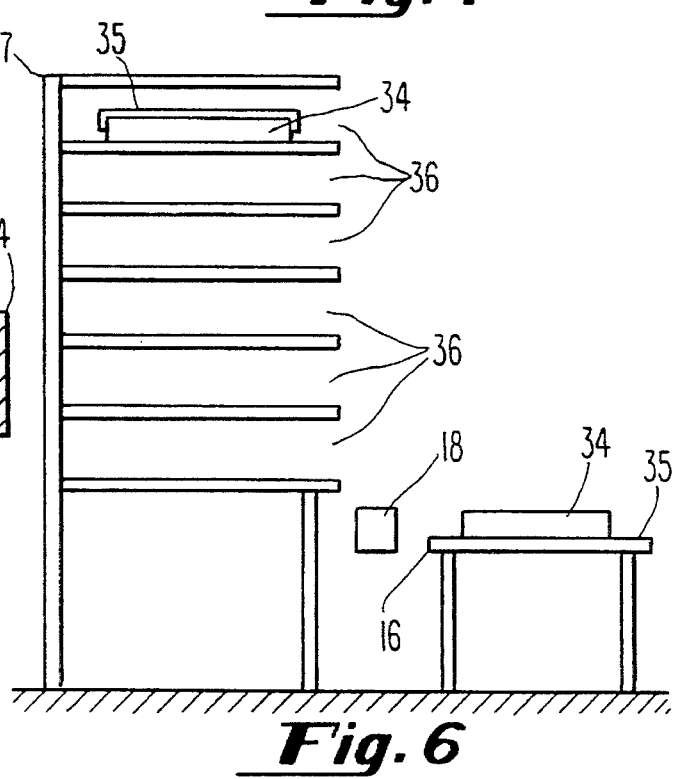
FIG. 6 is an elevation of an microtiter plate storage unit/and work station.

The arrangement of the microtiter plate storage unit 17 and work station 16 are shown in FIG. 6. As can be seen, each storage unit 17 is comprised of a number of compartments 36, each of which is adapted to hold a single microtiter plate 34 with its lid 35. The microtiter plate work stations 16 comprise a flat work surface 35 adapted to support an microtiter plate 34.

As shown in FIGS. 1, 4, and 6, pipet wash stations 18 are disposed adjacent the heating blocks 14 and microtiter plate work stations 16. The pipet storage units 19 are each comprised of a vertical array of storage compartments, similar to the microtiter plate storage unit 17, that are adapted to hold boxes of plastic disposable pipet tips 50 prior to their insertion onto the multichannel pipet hand 13, as shown in FIG. 8. The temperature controlled storage units 20 have doors 26 that are electrically operated by the robot controller 9. The temperature controlled storage units 20 have a vertical array of storage compartments each of which is adapted to hold two pairs of microtiter plates, each pair consisting of one microtiter plates stacked on another. The two pairs are stored next to one another. In the preferred embodiment, the storage units 20 are maintained at a temperature of 6° C. by the use of circulating cooled water. In addition, the storage units 20 may be equipped with a vacuum forming unit if it is desired to dry the reagents.

In the DNA sequencing method according to the current invention, Sequenase (available from US Biochemicals) Taq DNA polymerase (available form Perkins-Elmer Cetus) and Bst DNA polymerase (available from Bio-Rad) may be used for dideoxynucleotide DNA sequencing, although in principle almost any DNA polymerase may be used. Reaction conditions are based on the two-step reaction in which the initial extension of the primer and incorporation of radiolabeled nucleotide is performed as a separate step from the termination step. Radiolabeled dATP ($^{35}$S-dATP; $^{33}$P-dATP) (available from New England Nuclear) and solutions of deoxynucleosides and dideoxynucleotides (available from Boehringer Mannheim Biochemicals) may be used for this purpose. Optimal ratios of dideoxynucleotide to deoxynucleoside (Boehringer Mannheim) may be determined empirically. Products of sequencing reactions are separated on 6% DNA sequencing gels (Sequagel 6%; National Diagnostics) that are fixed in 10% methanol-10% acetic acid and dried under vacuum, and exposed to X-ray film to produce autoradiographs.

In the preferred embodiment, the system allows thirty micro-titer plates 34 and lids 35 to be stored at room temperature prior to sequencing and a maximum of forty plates with completed sequencing reactions to be stored in the cooled storage units 20. Therefore, the robot 2 can perform a maximum of 240 sequencing reactions (30 plates, 8 reactions per plate) in a single run. The system can, however, be configured to allow ambient, as well as cooled storage, of a maximum of sixty microtiter plates and, therefore, will allow a maximum of 480 reactions to be performed in a single unattended run.

Sequencing reactions, as performed manually, impose significant constraints on automation. The chief constraint is to pipet, reproducibly and precisely, volumes as small as 0.5 µl. However, pipetting, reproducibly and precisely, a volume of 0.5 µl is beyond the capacity of most automated pipetting systems.

One solution to this problem involves the use of dried reagents since they allow the use of larger volumes. The dried reagents in the target wells occupy no volume, therefore, the volume that is transferred can be larger by the volume that is normally occupied by the dried reagents. Use of dried reagents allows the use of volumes that for the smallest volumes are in the range of seven microliters, volumes that can be pipetted reproducibly and precisely by many automated systems. Consequently, the invention may be practiced by performing sequencing reactions using reagents dried under vacuum onto microtiter plates. In this case, the system would include cooled storage units 20 that could be placed under vacuum to dry down the reagents on microtiter plates. Such a system must: operate without intervention after the initial setup, have cooled storage that incorporated a robotically controlled lid for reagents, have cooled storage that could be placed under vacuum for microtiter plates, have several (preferably six or more) heat blocks sculpted to fit microtiter plates, be capable of manipulating microtiter plates and be capable of reproducibly pipetting volumes as small as seven microliters from microtiter plate wells containing as little as twelve microliters.

However, according to the current invention, the problems of pipetting small volumes may also be overcome by the use of surfactants along with a novel method of controlling the movement of the multichannel pipet hand 13 into the microtiter plate wells 40, thereby allowing the use of reagent solutions.

One of problems associated with pipetting small volumes of solutions is the tendency for droplets to bead up on the microtiter plates. The beading frequently results in failure to recover the desired volume from a well 40. Experiments to decrease the surface tension with non-ionic detergents indicate that a final concentration of 0.02% was adequate to prevent beading on polystyrene microtiter plates 34. However, the inventors have found that a concentration of 0.025% non-ionic detergents is not always adequate to prevent beading on the surface of the polypropylene inserts used in the reagent reservoirs 22. To consistently prevent beading of the solutions on the polypropylene surface it is necessary to increase the concentration of non-ionic detergents to at least 0.05.

Inclusion of the non-ionic detergents in all the reagents makes it possible for the robot to recover, reproducibly and precisely, seven microliters out of a total of 12 µl in each well 40 of a column of eight microtiter plate wells. In addition, it allows the robot to recover almost all of the reagents from the reservoirs 22, leaving as little as 20 µl.

According to the method on the current invention, the robot controls the movement of the multichannel piper hand 13 so that the pipet tips 50 touch the sides of the wells 40 while dispensing, so as to wipe the tips. Touching the sides provided a surface for the drops to run down, thereby preventing the solution from beading back onto the tip surface, since such beading would prevent all of the volume aspirated from being dispensed. Wiping of the tips resulted in increased reproducibility of the dispensed volume.

In the preferred embodiment, the operating system for the robot controller 9 utilizes an interpreted language with macro-like modules that can be nested to seven layers. Standard programming provided by the robot supplier may be used to control some basic functions that involve the coordination of power-and-event controller switches, such as the opening and closing of doors 26 of the temperature controlled storage units 20. However, software necessary to adequately control the robot's ability to pipet small volumes of about 7 µl volumes or less from source volumes of about 12 µl has not heretofore been available.

Although the multichannel micropipet hand 13 itself is capable of pipetting small volumes reproducibly and precisely if the pipet tips 50 are properly located within the well, the dexterity of the robot 2 in moving the multichannel micropipet hand 13 into the well 40 is crucial to accuracy. FIG. 8 shows the multichannel micropipet hand 13 suspended above a microtiter plate 34 just prior to insertion of the tips 50 into the wells 40 for aspiration. The inventors have found that accurate pipetting of small volumes from small source volumes requires that the pipet tips 50 reach to just above the bottoms of the microtiter plate wells 40. If the tips 50 are too high, they will not be immersed in the liquid for the last few microliters. If the tips 50 touched the bottoms of the wells with excessive force, however, the holes of the tips will be blocked and the recovery variable.

Unfortunately, because the robot's reach (i.e., from about 34 cm to about 70 cm depending on the hand) there is some sway or movement at the extremity of the arm 5. As a result, it is not possible to program the robot's movement to within the required sub-millimeter precision using absolute coordinates. This problem is solved in the current invention by programming the robot 2 so that it "senses" contact between the pipet tips 50 and the bottoms of the wells 40. Accordingly, the robot is equipped with force sensors 60, which may be of the strain gage type, that are coupled to the arm 5, as shown in FIG. 2. The sensors 60 provide a measure of the force exerted on the arm in arbitrary units. The feedback from the sensors 60 enables the arm 5 with the micropipet hand 13 to sense when the tips 50 make contact with the bottoms of the wells 40. After the tips 50 make contact, the height of the arm 5 is increased slightly to prevent the blockage of the tips.

Figure 10:
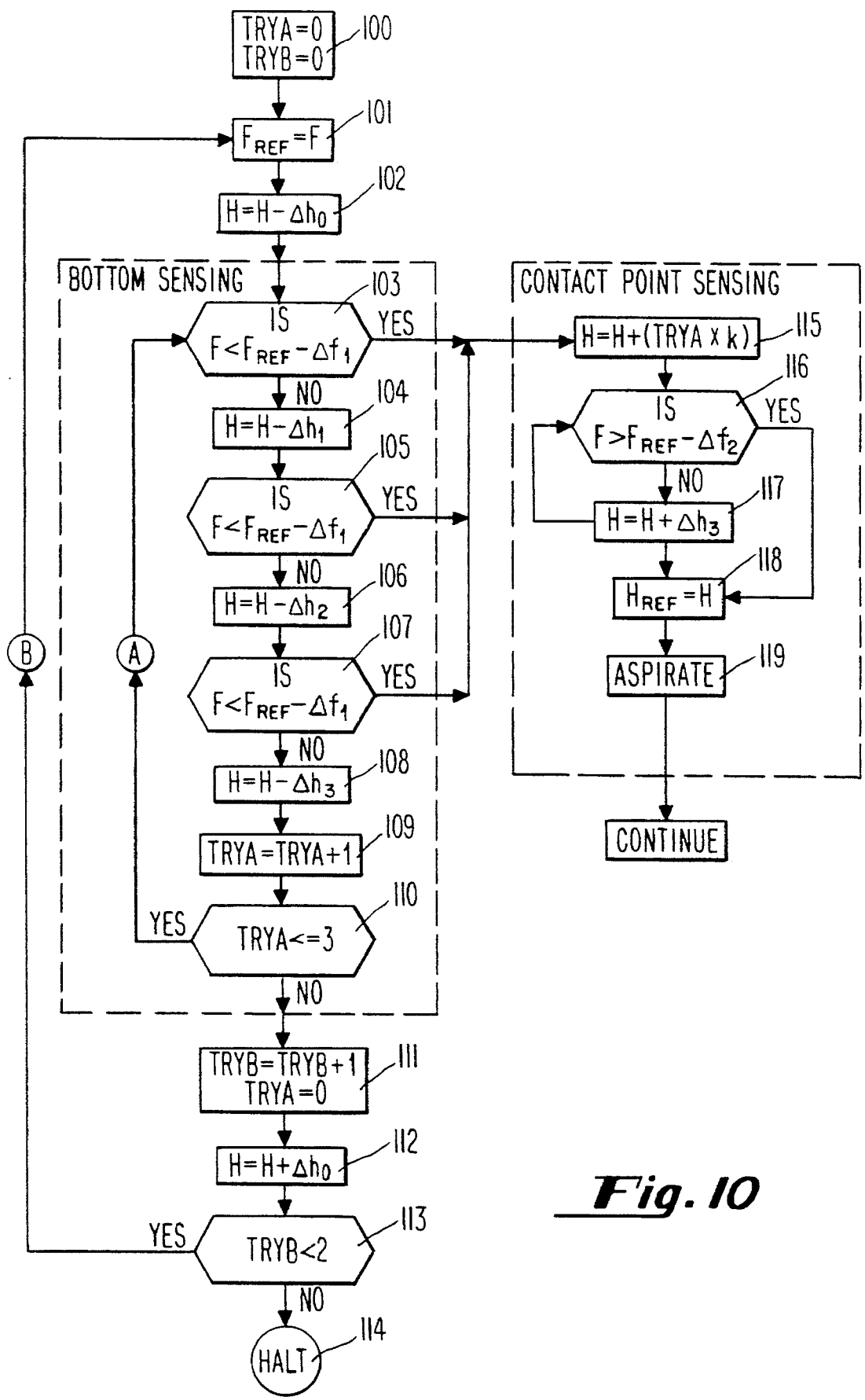
FIG. 10 is a flow chart of the pipet tip control method according to the current invention.

Unfortunately, the force sensors 60 lack precision and report variable readings depending on the recent movements of the arm 5. Specifically, the inventors have found that the value obtained from the force sensor 60 when the hand 13 is hanging freely is higher when the hand had recently been moved upward than when it had recently been moved downward. Also the sensitivity of the sensor 60 is insufficient to detect contact by an absolute measure. However, these limitations are overcome in the current invention by a novel pipet tip movement control method, a flow chart for which is shown in FIG. 10, for sensing when the tips 50 are at the appropriate location in the bottom of the wells 40 of a microtiter plate 34 for proper aspiration. This location, defined as the "contact point," is that location in which the pipet tips 50 almost touch the microtiter plate 34 so that the tips are not pressed against the bottoms of the wells, which would impede flow into them, nor are they so far above the bottoms of the wells as to prevent complete aspiration. The inventors have found that when the contact point is achieved, the microtiter plate can not be easily lifted from the sculptured surface of a heat block 14 but that the tips, which are somewhat flexible, do not show any signs of being subjected to force, such as bowing out. In additional, it has been found that when the contact point is achieved, it is possible to fractionally lift the microtiter plate off the heating block 14 if the height of the hand 13 were increased by 0.2 mm.

According to the pipet tip movement control method, the sensing of bottoms of the wells is refined by moving the pipet tips 50 toward the bottoms of the wells in a series of increasing smaller decrements in the height of the pipet tips above the wells 40, accomplished by a logic module referred to as "bottom sensing" in FIG. 10. Since the force sensed by the sensor 60 includes a force component attributable to the weight of the freely hanging multichannel piper hand 13, the measured force will decrease when the pipet tips 50 contact the bottoms of the well because the wells will then be supporting at least a portion of the weight of the hand. Therefore, each incremental decrease in height is alternated with a decision step that tests whether the force on the pipet tips, as measured by the sensor 60, is sufficiently small to indicate that the tips have contacted the bottoms of the wells.

Because of the insensitivity of the force sensors 60, described above, it is necessary that the force on the pipet tips 50 be sufficiently great to bow the tips outward in order to be assured that contact with the bottoms of the wells has occurred. Moreover, the point at which the tips are bowed is achieved incrementally to provide reproduciblity. Thus, the value that the measured force must be below, to satisfy the criteria for "bottom sensing" according to the method, is set so that at such a value of measured force, the pipet tips 50 can be expected to be bowed outward. However, reliable aspiration can not be achieved with the pipet tips pressing against the well bottoms with such force since their inlets are apt to be blocked by the contact. Consequently, after "bottom sensing," as determined above, is established, the height of the hand 13 is increased slightly until the measured force is sufficiently great to indicate that the pipet tips are almost contacting the bottoms of the well but without being subjected to appreciable force so that the hand 13 is essentially again hanging freely—this condition being the "contact point."

Of course this increase in height following bottom sensing must be sufficiently small or complete aspiration will not be achieved. Thus, according to the current invention, the raising of the hand 13 following bottom sensing is also done incrementally, in a logic module referred to as "contact point sensing" in FIG. 10.

The contact point sensing module lifts the arm in very small increments, the first of which is equal to the product of a small constant k times the number of loops, TRYA, through the bottom sensing module that were necessary to satisfy the "bottom sensing" condition. This incrementing is continued until the detected force is equal to the force sensed when the hand 13 was hanging freely, thereby indicating that the pipet tips are not pressing into the wells such that flow into them may be impeded.

Although the force with a freely hanging hand is measure just after the hand was suspended over the wells— that is, following a downward movement of the hand—due to the "history" phenomenon previously discussed, that measured force, defined as $F_{ref}$ in FIG. 10, will be greater than the force measured with a freely hanging hand that has been incremented upward during execution of the contact point sensing module. Consequently, a constant, $\Delta f2$, is subtracted from $F_{ref}$ to correct for the history effect in determining when the hand is hanging freely so that the contact point can be considered to have been reached in the contact point sensing module. In the preferred embodiment, the constant $\Delta f2$ is equal to the difference in the force measured with a freely hanging hand between a measurement taken after the hand was moved up and a measurement taken after the hand was moved down and need be established only once to account for the peculiarities of the particular robot system.

If the pipet tips fail to touch the bottoms of the wells after executing the bottom sensing module four times (three loops through route A in FIG. 10), the bottom sensing module is attempted from the beginning one more time (route B in FIG. 10). If they fail to touch the bottoms of the wells after an additional four passes through the bottom sensing module, the robot is halted.

Once the height necessary to achieve the "contact point" is determined, its value is stored and reused each time the hand 13 returns to that particular microtiter plate to aspirate another column of wells. Thus, the point of contact is determined only once for each set of eight sequencing reactions performed on a given microtiter plate. In the preferred embodiment, contact point sensing is determined for each microtiter plate when the column of wells containing the extended primer and template DNA together with the other reagents including the DNA polymerase are aspirated just prior to dispensing the reaction to the four termination mixes.

With specific reference to FIG. 10, the multichannel pipet control method of the current invention may be explained as follows. In step 100, the values of the counters TRYA and TRYB are zeroed after the hand 13 has moved into position above the microtiter plate as shown in FIG. 8. Note that to overcome the variability due to the effect of the recent history of the arm's movement on the force sensor 60 output, the force sensor is standardized by always moving toward and traversing the microtiter plate 34 in a similar manner—e.g., moving radially toward and across the plate—prior to beginning the method.

With the hand 13 suspended above the microtiter plate as shown in FIG. 8, the force F as sensed by the force sensor 60, which is equal to the force from a freely hanging hand after the hand has been moved downward, is measured and stored as $F_{ref}$ in step 101. In step 102, the height H of the multichannel pipet hand 13, which, as shown in FIG. 8, is initially poised just above the wells 40 of the microtiter plate 34, is incremented downward by a relatively large increment $\Delta h_0$. In step 103, the force F from the sensor 60 is measured again and it is determined whether or not this force is less than $F_{ref}$-$\Delta f_1$, $\Delta f_1$ being an empirically determined constant based on the particular robot, thereby indicating that bottom sensing has occurred. If it is less, the contact point sensing module is executed, as explained below. If it is not, then in step 104 the height H is incremented downward by a second increment $\Delta h_1$, $\Delta h_1$ being less than $\Delta h_0$, so that a smaller, finer increment is used in the second step down.

In step 105, the force F from the sensor 60 is measured again and it is again determined whether or not this force is less than $F_{ref}$-$\Delta f_1$. If it is less, the contact point sensing module is executed. If it is not, then in step 106 the height H is incremented down by a increment $\Delta h_2$, $\Delta h_2$ being less than $\Delta h_1$, so that a still smaller, finer increment is used in the third step down.

In step 107, the force F from the sensor 60 is measured again and it is determined whether or not this force is less than $F_{ref}$-$\Delta f_1$. If it is less, the contact point sensing module is executed. If it is not, then in step 108 the height H is incremented down by a increment $\Delta h_3$, $\Delta h_3$ being less than $\Delta h_2$ so that the bottom of the well 40 is approached with increasingly finer increments, and in step 109, TRYA is increased by one. In step 110, it is determined whether or not TRYA is less than or equal to three. If it is, then steps 103 to 110 are repeated, unless bottom sensing is achieved at some point through the module.

If TRYA is not less than or equal to three, then in step 111, TRYB is increased by one and TRYA set to zero. In step 112, the height is increased by the amount of the original decrement $\Delta h_0$ so that further execution of the bottom sensing module is begun with a height that is less than the original height by $4 \times (\Delta h_1 + \Delta h_2 + \Delta h_3)$. In step 113, it is determined whether or not TRYB is less than two. If it is, then steps 101 to 113 are repeated. If it is not, then the operation is halted and the problem investigated.

The contact point sensing module is initiated in step 115 by raising the height H of the arm by H+(TRYA× k), k being an empirically determined constant based on the particular robot. Thus, the amount by which the height of the hand 13 is raised—that is, the increase in height necessary to ensure that the tips 50 are not pressing against the wells with sufficient force to impede flow yet to also ensure that the tips are not moved so far from the bottom of the well that aspiration will be incomplete—is a function of the number of times the group of incrementing steps 104 to 108 were performed during the execution of the bottom sensing module that attained the contact point.

In step 116, the force F is measured again and it is determined if it is greater than $F_{ref}$-$\Delta f_2$, $\Delta f_2$ being an empirically determined constant to correct for the history effect, as previously discussed. If it not, then the height H is raised again by the increment $\Delta h_3$ and step 116 is repeated. If it is greater, then the value of $H_{ref}$ is set to H so that repetitions of the aspiration on the same microtiter plate can be repeated using the same height value determined above during the first aspiration on a particular microtiter plate. Lastly, in step 119 the aspiration of the contents of the wells 40 in the particular microtiter plate column are aspirated.

Empirically determined constants for height differences are about as follows: $\Delta h_0$ is slightly less than the height difference measured between the bottoms of the micropipet tips and the bottoms of the microtiter plate wells when the micropipet tip hand is in the position suspended over the wells. It is dependent on the definitions for the positions at and above the heating blocks 14, taught to the robot. The other empirical constants, $\Delta h_1$ to $\Delta h_3$, are in the submillimeter range, usually less than 0.1 mm, and initial values are used such that $\Delta h_2 = (1.7 \times \Delta h_3)$, and $\Delta h_1 = (2.5 \times \Delta h_3)$. For the empirically defined force constant $\Delta f_1$, the starting value is about equal to $\Delta f_2$ as defined above. All empirical values are refined by trials.

As can be readily appreciated, those skilled in the programming arts can readily program the logic discussed above and shown in FIG. 10 into a microprocessor of a robot controller, such as controller 9 shown in FIG. 1, so that the microprocessor provides the capability for performing the logic steps shown in FIG. 10.

One consequence of performing parallel reactions staggered by five minutes is that the time required to change micropipet tips 50 becomes rate limiting. To overcome the limitation, tip washing stations 18 are disposed adjacent those positions where the robot performs pipetting operations. For this purpose, plastic inserts are used similar to those used for the cooled reagent reservoir 22, except that the tip washing plastic inserts have a nominal volume of 38 ml, whereas the cooled reagent reservoir plastic insert have a nominal volume of 18 ml. The tip washing stations 18 are mounted such that they are radially in line with the microtiter plate and their upper edge is at the same height as the upper edge of a microtiter plate at the particular pipetting station, as shown in FIGS. 4 and 6.

Figure 9:
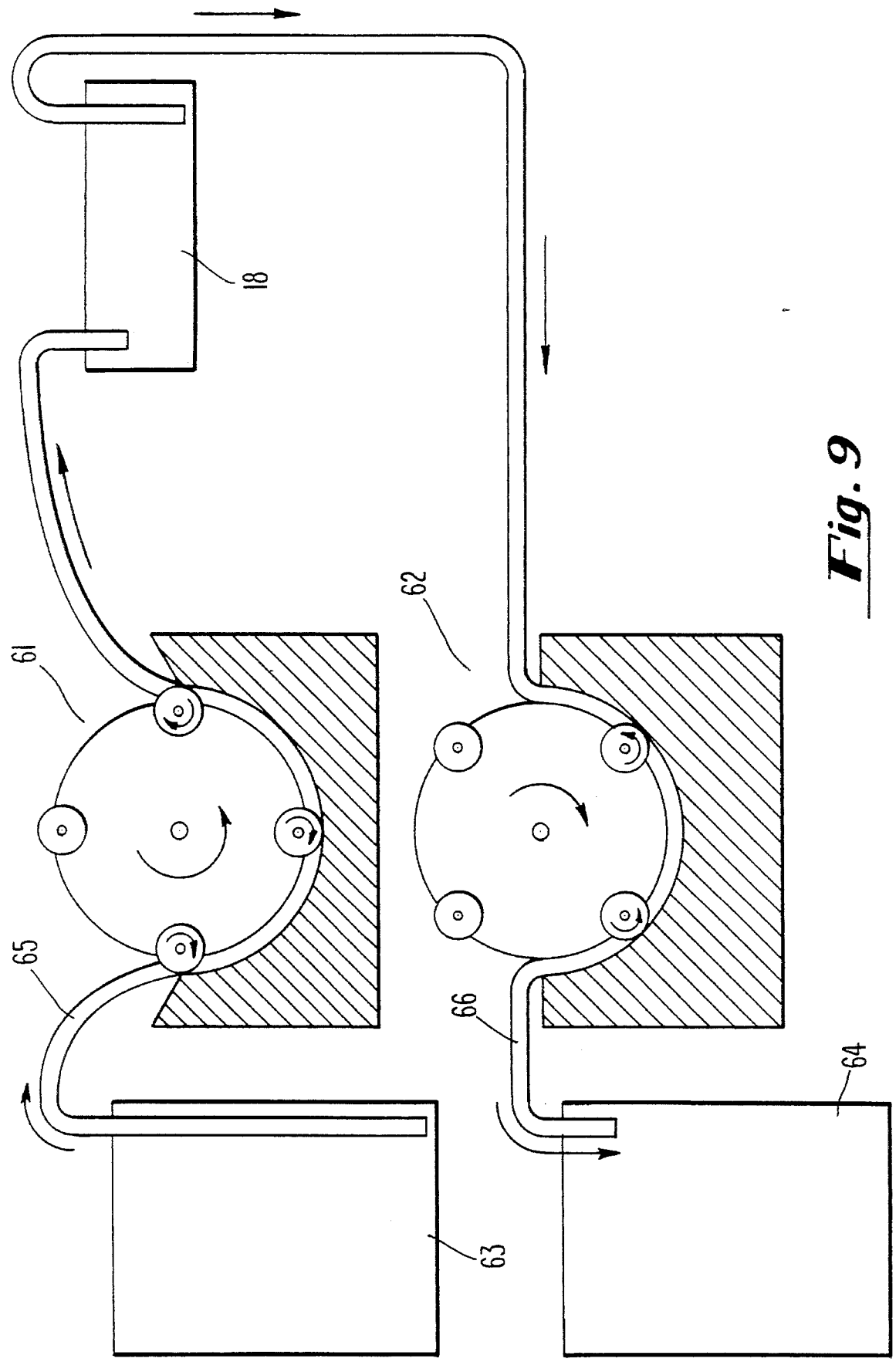
FIG. 9 is a schematic diagram of a peristaltic pump for one of the tip washing stations shown in FIG. 1.

When the tip washing station 18 is completely filled, it is possible to wash the tips without any additional adjustments with regard to rotational or vertical movement. A system driven by a peristaltic pumps 61 and 62, shown in FIG. 9, may be used to replenish the water in the tip washing stations 18 so as to maintain the volume at a constant level and prevent the accumulation of reagents during long runs may also be incorporated into the system. As shown in FIG. 9, in addition to the pumps 61 and 62, the system includes a source reservoir 63 and a waste reservoir 64, each in flow communication with a tip washing station 18 by means of hoses 65 and 66.

Tips are washed by aspirating and expelling 50 µl several times. To ensure that little or no water is transferred to the next reaction, with a resulting dilution of the reagents, the last expulsion of the washing solution is performed slowly while the tips are touching the side of and upper edge of the tip washing station to prevent beading of the water back onto the tips.

Another problem encountered when the microtiter plate format is used to facilitate automation of DNA sequencing according to the current invention is that evaporation of reagents occurs during the various heating steps in the reactions. This problem is solved in the current invention by the addition of non-ionic detergents containing water to compensate for volume loss due to evaporation, as explained further below.

The system can perform 240 reactions in a single unattended run of seven hours. However, the robot configuration can be altered to allow 480 reactions to be performed in an unattended run of fourteen hours. Therefore, if a daytime run of 240 reactions in seven hours is combined with a nighttime run of 480 reactions in fourteen hours, a total of 720 reactions could be performed per day.

The process of DNA sequencing consists of a series of steps: 1) preparation of the template, 2) performing reactions to generate a series of labeled, base-specific, randomly terminated fragments, 3) separation of the randomly-terminated fragments according to length, 4) detection of the separated fragments, and 5) interpretation of the information contained in the pattern of separated fragments. Automation of the steps results in greater throughput of sequences. Automation of all of the steps is essential for improved throughput in a single laboratory. Automation of the reactions necessary to generate the series of fragments is discussed in detail below.

In addition, preparation of DNA template can be performed with instruments such as the Biomek 1000 work station (available from Beckman) or Autogen 540 (available from Autogen). Detection of the separated fragments and interpretation of the information can be performed with fluorescence-based sequence detection systems coupled to computers such as the ABl-370 (available for Applied Biosystems), the A.L.F. (available from Pharmacia), or autoradiograph-based computer graphics systems such as that supplied by Bio-Rad or the Bio Image (available from Millipore) scanners and analysis systems. For further analysis of the information, many computer software packages are available.

The DNA sequencing method according to the current invention is begun by manually loading the reservoirs 22 with reagents. Enzyme plus label is placed in reservoir no. 1, terminations G, A, T and C, respectively, in reservoirs nos. 2–5, the STOP buffer in reservoir no. 6 and water in reservoir no. 7. Boxes of pipet tips 50 are manually loaded into the pipet storage units 19 and the DNA sample is manually deposited into the wells 40 of up to three microtiter plates 34. Because the samples are used eight at a time, one column at a time, and there are twelve columns on a microtiter plate 34, and because the maximum number of samples that can be processed in the preferred embodiment is 240 samples, up to three microtiter plates 34 containing samples may be placed on work surfaces of the robot. Two of the three microtiter plates may have all ninety six wells forty completely filled with samples and the third may have up to forty eight wells 40, wells in column 1 through column 6, filled.

In the preferred embodiment, more than one microtiter plate is used to increase the number of reactions performed in a set time. This is accomplished by programming the robot to perform two sets of reactions that are out of phase by five minutes, therefore, samples are deposited into the sample microtiter plates so that there are always even numbers of columns of samples. The reaction conditions for Bst DNA polymerase (see below) are modified such that each of the basic steps (i.e., heating or denaturation, annealing, labeling/extension and termination) are performed for about equal lengths of time— i.e., in blocks of about five minutes. Since all the sub-parts of the reactions are performed in blocks of the same length of time, two sets of reactions can be sequenced so that they are out of phase by one block (five minutes). That is, when the first sample is undergoing annealing, the second sample is undergoing denaturation, etc. In this manner, two sets of reactions can then be performed in twenty seven minutes. To accommodate the maximum number of plates in the cooled storage units 20, the robot 2 is programmed to stack one microtiter plate 34 on top of another prior to moving them to one of the temperature controlled storage units 20.

Once manual locating has been completed, automatic operation is then initiated. Interchanging the light weight and heavy weight hands 11 and 12 and the multichannel pipet hand 13, as required, the robot 2 steps through the sequence of operations programmed into the controller 9, performing the reactions on a pair of samples for each cycle, as explained above, and performing additional cycles until all of the samples have been sequenced. The light weight hand 11 is used to move boxes of micropipet tips 50 from the micropipet tip storage units 19 and to move microtiter plates 34 from microtiter plate storage units 17. The heavy duty hand is used to manipulate microtiter plates 34 and lids 35, when they are on the heating blocks 14 and especially when the microtiter plates 34 with lids 35 are stacked on one another and moved to the temperature controlled storage units 20.

In the first step, the robot 2 using the light weight hand 11 removes a box of tips 50 from the tip storage 19 and places it on the tip work station 15. All of the sample plates are first placed in the temperature controlled storage unit 20 using the heavy duty hand 12. The first microtiter plate 34 containing samples is then placed on a work station 16. Next, using the light duty hand 11, two empty microtiter plates 34 are removed from a microtiter plate storage unit 17 and placed on each of two of the heater blocks 14 in the outer row of heating blocks and the lids 35 of the microtiter plates are removed and placed on an adjacent work station 16 or a heating block 14. Note that the system 1 incorporates an outer row of heating blocks 14, in addition to an inner row, so that heating can be carried out at two temperatures. However, in the preferred embodiment of the method, heating is only necessary at one temperature so that the outer row of heating blocks 14 function merely as work stations and do not produce heat. The lid of the microtiter plate containing samples on work station 16 is removed and placed on an adjacent work station 16.

Using the multichannel pipet 13, the robot aspirates one column of wells 40 from the sample containing microtiter plate on the work station 16 and dispenses them into the first column of one of the empty microtiter plates on the outer row of heating blocks. The tips 50 are then washed in the tip washing station 18. These steps are repeated so that the first column of the second, previously empty, microtiter plate on the outer row of heating blocks is also filled with sample.

Next, the lids of the microtiter plates on the heating blocks are replaced and one of the microtiter plates from the outer row of heating blocks is placed on an active heating block 14 in the first row, whereupon it is heated for five minutes at 65° C. to complete the denaturation step. The lid of the microtiter plate that contained samples is replaced and the microtiter plate is then returned from work station 16 to the storage unit 20 if there are still samples remaining on the microtiter plate. If no samples are remaining, the microtiter plate is disposed of to free up the work station 16. The other microtiter plate from the outer row of heating blocks is placed in the storage unit 20. As previously discussed, these two microtiter plates are processed so that one of the basic steps on each is followed by one of the basic steps on the other. However, for simplicity, the method will be described from beginning to end with respect to only one microtiter plate without interrupting the explanation to discuss the out of phase reaction being performed on the second microtiter plate.

The microtiter plate containing the now denatured sample is then placed on a work station 16 where it is held at room temperature for five minutes to complete the annealing step. Its lid is removed and placed on an adjacent work station 16.

During the time that the annealing is taking place while the plate the microtiter plate is at room temperature, the reagents are aspirated from the reservoirs 22 and dispensed into the microtiter plate containing the denatured sample. First, the STOP buffer is dispensed into column no. 6, followed by tip washing in the tip washing station 18. The water is then aspirated and dispensed from its reservoir 22 into column no. 7 of the microtiter plate and the tips are again washed. In sequence, the terminations G, A, T, and C are then aspirated from their reservoirs 22 and dispensed into column nos. 2–5 of the microtiter plate, with the tips being washed between each operation. Following these steps, the tips 50 are disposed of in the tip disposal unit 30 and a new set of tips from the tip work station 15 are placed on the multichannel pipet 13.

Next, the enzyme/label is aspirated from its reservoir 22 directly into the DNA sample in column no. 1 of the microtiter plate. The lid of the microtiter plate is replaced and the microtiter plate is then placed on one of the active heating blocks 14 to begin the five minute label and extension step while being heated to 65° C. After five minutes the lid of the microtiter plate is removed to an adjacent heating block 14 and the reaction volume in column 1 is supplemented with the water from column 7 by aspirating water from column 7 and dispensing into column 1. The five minute termination step is then begun by sequentially pipetting portions of sample from column no. 1 of the microtiter plate into columns nos. 2–5 containing the G, A, T and C terminations. The lid of the microtiter plate is replaced for the five minute incubation. After five minutes, the lid is removed to an adjacent heating block and portions of the STOP buffer are then aspirated from column no. 6 into each of columns nos. 2–5 to stop the reactions. After the addition of the STOP buffer to the termination reactions, the lid is replaced and the microtiter plate is moved to an adjacent heating block that is at room temperature while the reactions in the other microtiter plate in the pair is completed. This microtiter plate is then stacked on top of the other microtiter plate in a pair, which by now has also been processed in the sequential, out of phase method previously discussed, and both are stored in the storage unit 20 while the second pair of samples are processed. Processing and storing of successive pairs of samples is continued until all of the samples are sequenced. When the micropipet tips 50 in a box in the tip station 15 are depleted the empty box is disposed of by returning it to a rack in a tip storage 19. A new box of micropipet tips 50 is then moved from the tip storage 19 to the tip station 19.

Following sequencing, the samples are placed on a sequencing gel the gels are electrophoresed, fixed, dried and X-rayed film is exposed to it to generate an autoradiogram to identify the DNA sequence using techniques well known in the art.

Sequenase is an enzyme that has become a standard for sequencing in many laboratories. To compare the sequencing reactions performed by the robot with those performed routinely in other laboratories, the reaction conditions for Sequenase were modified for use on the robot. DNA and primer were heated to 65° C. for five min., the primer was annealed to the DNA at room temperature for four min., the enzyme-labeling mix was added and the reaction incubated for four minutes at room temperature, the extension-reaction products were dispensed into the termination mixes and the reactions were incubated at 37° C. for five min. Sequencing reactions were stopped by the addition of STOP buffer. Because of the constraints on pipetting, the volumes of the reactions had to be increased. When microtiter plates were incubated at 65° C., there was loss of volume due to evaporation even though the plates were covered with lids at all times except during pipetting. Therefore the annealing volume was increased to 16 µl as compared with 10 µl in the standard protocol. After annealing the effective volume was about 10 µl. The buffer in the annealing mix was adjusted to be correct for the effective volume. The enzyme-labeling mix was essentially identical to the standard protocol except that non-ionic detergents were added to a final concentration of 0.02% and the volume of enzyme dilution buffer was about one-third of the standard protocol. After the labeling-extension reaction was complete, the volume was increased by the addition of 9 µl of water to about 25 µl. Five microliters of the labeling-extension reaction was dispensed to each of the 5 µl termination mixes. The reaction was terminated by the addition of four µl STOP buffer.

The sequences generated were comparable to those generated by an individual experienced at sequencing. Furthermore, there was little if any variation from well to well, and from plate to plate for a single template.

Sequenase is, however, labile. The manufacturer recommends not storing the diluted enzyme for more than 60 min. at 4° C. To achieve the goal of long periods of unattended operation, it was essential to use an enzyme that was stable in solution at 4° C. at the working dilution. The DNA polymerase from *Bacillus stearothermophilus* (Bst DNA polymerase) is reported to be extremely stable and is functional for sequencing even after fourteen days of storage at room temperature. Therefore, we investigated its use for the robot. The sequencing conditions were similar to those developed for the use of Sequenase with the robot except that all steps were performed for about five minutes and the elongation-labeling and termination steps were performed at 65° C. It was therefore necessary to compensate for greater loss of volume due to evaporation (See Table). Denaturation was performed with a starting volume of 22 µl. After annealing the volume was about 16 µl and seven µl of enzyme-labeling mix was added. Evaporation during extension resulted in loss of about seven µl. Twenty µl of water (that included the non-ionic detergents to 0.05% detergents) was added prior to dispensing seven µl to each of the termination mixes. Evaporation resulted in a final volume of about seven µl for each termination reaction. The reaction was stopped by the addition of five µl STOP buffer.

Bst DNA polymerase gave excellent results and was stable in the reagent reservoir for at least 24 hours.

TABLE

| Volumes (in µl) of Sequencing Reactions During Different Segments | | | |
|---|---|---|---|
| | Sequenase | | Bst DNA pol. |
| | Standard | Robot | Robot |
| Annealing Reaction | | | |
| Annealing mix | 10 | 16 | 22 |
| Starting volume | 10 | 16 | 22 |
| [Evaporation] | — | −6 | −6 |
| | 10 | 10 | 16 |
| Labeling-Extension Reaction | | | |
| Enzyme-labeling mix added | +5.5 | +6 | +7 |
| Starting volume | 15.5 | 16 | 23 |
| [Evaporation] | — | — | −7 |
| | 15.5 | 16 | 16 |
| Volume added to compensate for evaporation | — | 9 | 20 |
| | 15.5 | 25 | 36 |
| Volume dispensed (total) | 14 | 20 | 28 |

TABLE-continued

Volumes (in μl) of Sequencing Reactions During Different Segments

|  | Sequenase | | Bst DNA pol. |
| --- | --- | --- | --- |
|  | Standard | Robot | Robot |
| per termination (4 times) Termination Reaction | 3.5 | 5 | 7 |
| Termination mix | 2.5 | 5 | 7 |
| Dispensed elongation reaction | +3.5 | +5 | +7 |
| [Evaporation] | 6 | 10 | 14 |
|  | — | −2 | −7 |
| Addition of STOP Buffer | 6 | 8 | 7 |
| STOP Buffer | +4.0 | +4 | +4 |
| Final vol/termination reaction | 10.0 | 12 | 11 |

The system according to the current invention could also be used in a diagnostic DNA sequencing laboratory, where speed, quality, and reproducibility are of paramount importance. Analysis of the sequences of the same gene or cDNA fragments from different patients makes it possible to produce rapidly large numbers of DNA sequencing templates especially if the PCR is employed. In addition, the demonstrated low-volume pipetting dexterity could be employed for sequencing with non-radioactive labels, as well. Use of fluorescent tags would accommodate those DNA sequencing projects or facilities that utilize automated detection systems. Accordingly, the present invention may be embodied in other specific forms without departing from the spirit or essential attributes thereof and, accordingly, reference should be made to the appended claims, rather than to the foregoing specification, as indicating the scope of the invention.

What is claimed is:

1. A robotic system for automatically performing DNA sequencing, comprising:

a robot having an arm mounted for motion in vertical and horizontal planes;

a hand for said robot arm having means for pipetting a fluid from a microtiter plate well;

a microtiter plate having a well formed therein, said well having a bottom, a reagent solution contained in said well;

a plurality of work surfaces, each having means for supporting a microtiter plate;

a plurality of reservoirs, each having means for holding a reagent;

first storage means for storing microtiter plates;

sensing means for generating a signal in response to said pipetting means making contact with said microtiter plate well bottom; and a programmable controller having (i) first logic means for instructing said robot to move said pipetting means toward said microtiter plate well bottom by a series of discrete incremental movements, each of said discrete incremental movements in said series being separated by a finite period of time, said series of incremental movements including a set of incremental movements in which each discrete incremental movement is successively smaller than each previous discrete incremental movement in said set, and (ii) second logic means for determining whether said pipetting means has made contact with said microtiter plate well bottom based on said signal from said sensing means during said finite period of time between each of said discrete incremental movements in said set of movements.

2. The robotic system according to claim 1, wherein said first logic means further comprises means for instructing said robot to move said pipetting means toward said microtiter plate well bottom by at least one additional set of incremental movements, each incremental movement in any such additional sets being successively smaller than each previous incremental movement in its respective set, additional sets of incremental movements being successively performed until said second logic means has determined that said pipetting means has contacted said microtiter plate well bottom.

3. The robotic system according to claim 1, wherein said set of incremental movements comprises at least three incremental movements.

4. The robotic system according to claim 1, wherein said sensing means comprises means for sensing a force acting on said hand, and wherein said second logic means comprises:

means for instructing said robot to sense an initial force acting on said hand prior to said set of incremental movements;

means for determining if said force sensed differs from said initial force by more than a first predetermined value after each of said incremental movements in said set of movements.

5. The robotic system according to claim 4, wherein said first predetermined value is approximately equal to the difference in said forced sensed when said hand is hanging freely from said robot arm immediately after said hand has been moved in a downward direction and said force sensed when said hand is hanging freely from said robot arm immediately after said hand has been moved in an upward direction.

6. The robotic system according to claim 1, wherein said reagent solution contained in said well includes a non-ionic surfactant.

7. The robotic system according to claim 6, wherein said non-ionic surfactant in said reagent solution has a concentration of at least 0.02%.

8. The robotic system according to claim 6, wherein said non-ionic surfactant in said reagent solution has a concentration of about 0.02%.

9. The robotic system according to claim 1, further comprising means for holding and heating said microtiter plate.

10. The robotic system according to claim 9, wherein said pipetting means comprises a plurality of pipet tips capable of being coupled and uncoupled from said hand.

11. The robotic system according to claim 10, further comprising:

means for storing said pipet tips;

means for storing a plurality of empty microtiter plates; and means for heating said microtiter plate.

12. The robotic system according to claim 11, wherein said means for holding and heating said microtiter plate, said work surfaces, said reservoirs, and each of said storage means are arranged in a approximately circular array, and wherein said robot is centrally disposed within said array.

13. The robotic system according to claim 9, wherein said microtiter plate well defines a surface through which heat can flow into said well, and wherein said means for holding and heating said microtiter plate has a heat transfer surface formed therein that conforms to said microtiter plate well surface.

14. The robotic system according to claim 10, further comprising means for washing said pipet tips.

15. The robotic system according to claim 1, wherein said programmable controller has third logic means for instructing said robot to move said pipetting means away from said microtiter plate well bottom to allow aspiration of substantially all of said reagent solution from said microtiter plate well after said second logic means has determined that said pipetting means has made contact with said microtiter plate well bottom.

16. The robotic system according to claim 15, wherein said third logic means comprises means for instructing said robot to move said pipetting means in a direction away from said microtiter plate well bottom by a succession of incremental movements until said means for determining whether said pipetting means is still in contact with said microtiter plate well bottom has determined that said pipetting means is not still in contact with said microtiter plate well bottom.

17. The robotic system according to claim 15, wherein said third logic means comprises:

means for instructing said robot to move said pipetting means in a direction away from said microtiter plate well bottom by a first predetermined increment; and means for determining whether said sensed has changed by more than a second predetermined pipetting means is still in contact with said microtiter plate well bottom after said pipetting means has been moved away from said plate well bottom by said first predetermined increment.

18. The robotic system according to claim 17, wherein:

said first logic means further comprises means for instructing said robot to move said pipetting means toward said microtiter plate well bottom by at least one additional set of incremental movements, each incremental movement in any such additional sets being successively smaller than each previous incremental movement in its respective set, additional sets of incremental movements being performed in succession until said second logic means has determined that said pipetting means has contacted said microtiter plate well bottom; and the value of said first predetermined increment is variable, said third logic means having means for varying the magnitude of said first predetermined increment as a function of the number of said sets of incremental movements performed.

19. The robotic system according to claim 18, wherein said third logic means has means for varying the magnitude of said first predetermined increment so that said first predetermined increment increases as the number of said sets of incremental movements performed increases.

20. The robotic system according to claim 17, wherein said sensing means comprises means for sensing a force acting on said hand, and wherein said means for determining whether said pipetting means is still in contact with said microtiter plate well bottom further comprises:

means for instructing said robot to sense an initial force acting on said hand prior to said movement by said first predetermined increment; and means for determining if said force sensed differs from said initial force by more than a first predetermined value after said pipetting means has been moved by said first predetermined increment.

21. The robotic system according to claim 20, wherein said first predetermined value is approximately equal to the difference in said forced sensed when said hand is hanging freely from said robot arm immediately after said hand has been moved in a downward direction and said force sensed when said hand is hanging freely from said robot arm immediately after said hand has been moved in an upward direction.

22. A robotic system for automatically performing reactions in sequence, comprising:

means for containing a fluid, said fluid containing means having a bottom;

a robot having means for drawing a fluid from said fluid containing means, said fluid drawing means normally spaced from said fluid containing means bottom by a distance;

means for causing relative motion between said fluid containing means and said fluid drawing means;

sensing means for generating a signal in response to said fluid drawing means making contact with said bottom of said fluid containing means; and a programmable controller having (i) first logic means for instructing said relative motion causing means to reduce said distance between said bottom of said fluid containing means and said fluid drawing means by a series of discrete incremental movements, each of said discrete incremental movements in said series being separated by a finite period of time, said series of discrete incremental movements including a set of discrete incremental movements in which each discrete incremental movement is successively smaller than each previous discrete incremental movement in said set, and (ii) second logic means for determining whether said fluid drawing means has made contact with said bottom of said fluid containing means based on said signal from said sensing means during said finite period of time between each of said discrete incremental movements in said set of movements.

23. The robotic system according to claim 22, wherein said sensing means comprises means for sensing a force acting on said fluid drawing means, and wherein said second logic means comprises:

means for instructing said robot to sense an initial force acting on said fluid drawing means prior to said set of incremental movements;

means for determining if said force sensed differs from said initial force by more than a first predetermined value after each of said incremental movements in said set of movements.

24. The robotic system according to claim 22, wherein said programmable controller has third logic means for instructing said relative motion causing means to move said fluid drawing means in a direction away from said bottom of said fluid containing means by a first predetermined increment after said second logic means has determined that said fluid drawing means has made contact with said bottom of said fluid containing means.

25. The robotic system according to claim 24, wherein said third logic means comprises means for determining whether said fluid drawing means is still in contact with said bottom of said fluid containing means after said fluid drawing means has been moved in said direction away from said bottom of said fluid containing means by said first predetermined increment.

26. The robotic system according to claim 25, wherein said sensing means comprises means for sensing a force acting on said fluid drawing means, and wherein said means for determining whether said fluid drawing means is still in contact with said bottom of said fluid containing means further comprises:

means for instructing said robot to sense an initial force acting on said fluid drawing means prior to said movement by said first predetermined increment; and means for determining if said force sensed differs from said initial force by more than a first predetermined value after said fluid drawing means has been moved by said first predetermined increment.

* * * * *

UNITED STATES PATENT AND TRADEMARK OFFICE
CERTIFICATE OF CORRECTION

PATENT NO. : 5,455,008
DATED : October 3, 1995
INVENTOR(S) : Earley et al.

It is certified that error appears in the above-indentified patent and that said Letters Patent is hereby corrected as shown below:

Col. 6, Line 10, after "0.05" please insert therefore -- % --.

Col. 7, Line 36, please delete the word "piper" and insert therefore -- pipet --.

Signed and Sealed this

Twenty-eighth Day of May, 1996

Attest:

BRUCE LEHMAN

*Attesting Officer*   *Commissioner of Patents and Trademarks*